United States Patent
Jau et al.

(10) Patent No.: US 6,693,194 B2
(45) Date of Patent: Feb. 17, 2004

(54) PROCESS FOR THE PREPARATION OF 4,6-DIMETHOXY-2-(METHYLSULFONYL)-1,3-PYRIMIDINE

(75) Inventors: Beat Jau, Münchwilen (CH); Bernhard Urwyler, Schweizerhalle (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/332,248

(22) PCT Filed: Jul. 19, 2001

(86) PCT No.: PCT/EP01/08373

§ 371 (c)(1),
(2), (4) Date: Jan. 6, 2003

(87) PCT Pub. No.: WO02/08207

PCT Pub. Date: Jan. 31, 2002

(65) Prior Publication Data

US 2003/0135047 A1 Jul. 17, 2003

(30) Foreign Application Priority Data

Jul. 21, 2000 (CH) ................................................ 1439/00

(51) Int. Cl.⁷ .......................................... C07D 239/60
(52) U.S. Cl. ...................................................... 544/302
(58) Field of Search ........................................ 544/302

(56) References Cited

U.S. PATENT DOCUMENTS 4,711,959 A   12/1987  Kluth et al. ................. 544/320
5,149,357 A    9/1992  Dixson ........................ 544/300

FOREIGN PATENT DOCUMENTS

| EP | 0 209 779 A2 | 1/1987 |
| JP | 64-40470 | 2/1989 |
| WO | 00/46213 | 8/2000 |

OTHER PUBLICATIONS

Koppel, HC et al., "Pyrimidines. I. Synthesis of Pyrimidinethiols", J. Org. Chem., vol. 26 (1961), pp. 792–803.

Nezu, Y et al., "Dimethoxypyrimidines as Novel Herbicides. Part 2. Synthesis and Herbicidal Activity of O–Pyrimidinylsalicylates and Analogues". Pestic. Sci., vol. 47 (1996), pp. 115–124.

*Primary Examiner*—John M. Ford
(74) *Attorney, Agent, or Firm*—Thomas Hamilton

(57) ABSTRACT

Process for preparing 4,6-dimethoxy-2-(methylsulfonyl)-1,3-pyrimidine by reacting 4,6dichloro-2-(methyltio)-1,3-pyrimidine in an inert organic solvent with an alkali metal methoxide, transfer of the resulting 4,6-dimethoxy-2-(methylthio)-1,3-pyrimidine into an aqueous-acidic medium and subsequent oxidation of this compound, of appropriate in the presence of a catalyst, wherein the oxidation is followed by a purification step in which the aqueous-acidic reaction mixture is adjusted with aqueous base to a pH in the range of 5–8 and stirred either in the presence or in the absence of an organic solvent, and the use of this compound for preparing herbicides, for example 7-[(4,6-dimethoxypyrimidin-2-yl)thio]-3-methylphthalide.

23 Claims, No Drawings

PROCESS FOR THE PREPARATION OF 4,6-DIMETHOXY-2-(METHYLSULFONYL)-1,3-PYRIMIDINE

This application is a 371 of International Application No. PCT/EP01/08373, filed Jul. 19, 2001, the contents of which are incorporated herein by reference.

The invention relates to a novel process for preparing by-product-free 4,6-dimethoxy-2-(methylsulfonyl)-1,3-pyrimidine and to its use as an intermediate in the preparation of herbicidal 7-[(4,6-dimethoxypyrimidin-2-yl)thio] naphthalide derivatives.

Processes for preparing 2-alkylsulfonylpyrimidine derivatives which are disubstituted, in the 4- and 6-position, are already known from EP-A-0 209 779, J. Org. Chem. 26, 792 (1961) and Pestic. Sci. 47, 115 (1996). Some of the processes described proceed in a complicated manner via a plurality of discrete reaction steps, with isolation of the respective intermediates. Thus, for example, the first two documents describe the oxidation to the corresponding 2-alkylsulfonyl-pyrimidine derivatives by introduction of chlorine gas into a two-phase system (Example II-1, page 15) or an absolute alcoholic solution of 2-alkylthiopyrimidine derivatives (example 4,6-dichloro-2-(methylsulfonyl)pyrimidine (compound XXXVII), page 802). Pestic. Sci. describes both the reaction of 4,6-dichloro-2-(alkylthio)-1,3-pyrimidine with sodium alkoxide to the corresponding 4,6-dialkoxy-substituted 2-alkylthio-pyrimidine derivatives and its oxidation to the corresponding 4,6-dialkoxy-2-(alkylsulfonyl)-1,3-pyrimidines with Oxone or hydrogen peroxide and sodium tungstate as catalyst. The pure end product is prepared by recrystallization. However, the observed yields and purities of the products are frequently unsatisfactory for industrial preparation processes. Moreover, the isolation and purification procedures are uneconomical and associated with a high expenditure on apparatus.

It is an object of the present invention to eliminate these disadvantages and to provide a more simple process which is suitable for industrial applications. Surprisingly, it has now been found that 4,6-dimethoxy-2-(methylsulfonyl)-1,3-pyrimidine can be prepared in a simple manner, in high yield and purity, in an economically and ecologically particularly advantageous manner from 4,6-dichloro-2-(methylthio)-1,3-pyrimidine by reacting the latter compound with an alkali metal methoxide and oxidizing the resulting 4,6-dimethoxy-2-(methylthio)-1,3-pyrimidine without isolation directly to the corresponding 2-methylsulfonylpyrimidine derivative and freeing this in a subsequent purification step in the same reaction vessel as a "one-pot reaction" from any by-products formed, allowing direct use, for example, for preparing herbicides according to EP-B-0 447 506.

Accordingly, the present invention provides a process for preparing 4,6-dimethoxy-2-(methylsulfonyl)-1,3-pyrimidine by reacting 4,6-dichloro-2-(methylthio)-1,3-pyrimidine in an inert organic solvent with an alkali metal methoxide, transfer of the resulting 4,6-dimethoxy-2-(methylthio)-1,3-pyrimidine into an aqueous-acidic medium and subsequent oxidation of this compound, if appropriate in the presence of a catalyst, wherein the oxidation is followed by a purification step in which the aqueous-acidic reaction mixture is adjusted with aqueous base to a pH in the range of 5–8 and stirred either in the presence or in the absence of an organic solvent.

In the first step (Reaction Scheme 1), the reaction of 4,6-dichloro-2-(methylthio)-1,3-pyrimidine with the alkali metal methoxide is expediently carried out in an inert organic solvent such as a hydrocarbon, for example an aromatic hydrocarbon such as benzene, toluene or the isomeric xylenes, preferably in toluene, at reaction temperatures of from 0° C. to the boiling point of the solvent used, preferably at temperatures of from 20° to 60° C.

The alkali metal methoxide used is preferably sodium methoxide or potassium methoxide and particularly preferably a 30% sodium methoxide solution in methanol or solid sodium methoxide (for example 95%), where from 2 to 3 molar equivalents, preferably from 2.05 to 2.50 molar equivalents, of methoxide are used for the substitution reaction, based on 1 mol of 4,6-dichloro-2-(methylthio)-1,3-pyrimidine. Expediently, the methoxide solution or the solid methoxide is added dropwise or added, respectively, in the temperature range stated within a period of 2–6 hours to a solution of 4,6-dichloro-2-(methylthio)-1,3-pyrimidine which has initially been charged, and the reaction mixture is then stirred for from 5 to 10 hours or until no more starting material can be detected, at temperatures of from 50° to 60° C.

After this reaction time, the resulting mixture is prepared for the oxidation in the second step. To optimize the product yield, some of the methanol present in the reaction mixture may first be distilled off under reduced pressure, the distillation being terminated once 50–90% of the total amount of methanol has been distilled off. Water and a water-immiscible azeotrope-forming inert organic solvent, for example toluene, are then added to the resulting reaction mixture, and the entire mixture is heated with stirring to from 30° to 80° C., preferably from 30° to 60° C. After cooling, the aqueous phase is separated off and, to optimize the yield, once more admixed with the inert organic solvent and heated with stirring to from 30° to 80° C., preferably from 30° to 60° C. After cooling, the aqueous phase is separated off and discarded and the two organic phases are combined and substantially evaporated under reduced pressure. Water, heated to from 40° to 80° C., is added to the resulting residue, and the complete remainder of the organic solvent is distilled off azeotropically, until only water can be detected in the distillate.

The oxidation of the resulting and prepared 4,6-dimethoxy-2-(methylthio)-1,3-pyrimidine in the second step (Reaction Scheme 1) is expediently carried out in a protic solvent or a protic solvent mixture and, depending on the oxidizing agent used, if appropriate in the presence of a catalyst. Thus, expediently, a concentrated acid such as a carboxylic acid, for example 100% acetic acid, is added to the prepared aqueous reaction mixture from the first step, until a 1–80%, preferably 2–10%, aqueous solution of the corresponding carboxylic acid is obtained. To this end, depending on the oxidizing agent used, 0.1–0.2 mol % of a catalyst, based on 4,6-dimethoxy-2-(methylthio)-1,3-pyrimidine, such as a tungstate, for example sodium tungstate, is added, and this mixture is heated to from 70° to 90° C., preferably from 75° to 80° C. From 2 to 4 mol, preferably from 2.1 to 3 mol, of an oxidizing agent, such as a peroxide, for example 20–35% hydrogen peroxide solution, based on 4,6-dimethoxy-2-(methylthio)-1,3-pyrimidine, are then added dropwise. The exothermic oxidation reaction is maintained at the stated reaction temperature for 1–6 hours or until all of the methylthiopyrimidine or methylsulfoxide pyrimidine has been oxidized to the methylsulfonylpyrimidine.

After the oxidation has ended, excess oxidizing agent present in the reaction mixture is destroyed in a customary manner, known to the person skilled in the art, for example by adding 40% aqueous sodium hydrogen sulfite solution to the reaction mixture until no more oxidizing agent can be detected (potassium iodide/starch test), and the reaction mixture treated in this manner is prepared for the subsequent purification step which is carried out in the same reaction vessel.

One feature of the reaction sequence according to the invention is the purification step which follows as a "one-pot reaction" in the same reaction vessel and which offers great advantages for industrial processes since complicated separation and purification steps can be avoided and the expenditure on apparatus can be reduced.

To this end, the aqueous-acidic reaction mixture obtained in the preceding two-step reaction sequence is first adjusted with an aqueous base at temperatures of from 10° to 90° C. to a pH in the range from 5–8 and then either according to Variant A) this resulting aqueous phase is stirred in the temperature range of from 10° to 90° C. and at the stated pH for from 0.5 to 5 hours, or Variant B) is admixed with a water-immiscible inert organic solvent such as an aromatic hydrocarbon, for example benzene, toluene or the isomeric xylenes, and the resulting two-phase system is stirred, if appropriate with addition of a phase-transfer catalyst, in the temperature range of from 100 to 90° C. and at the stated pH for from 0.5 to 5 hours, or Variant C) is admixed with a water-miscible organic solvent, for example an alcohol, thus generating an aqueous-organic one-phase system which is stirred in the temperature range from 10° to 90° C. and at the stated pH for from 0.5 to 5 hours.

During this step, the by-products, formed in an amount of <10%, specifically 2,4-bis(methylsulfonyl)-6-methoxy-1,3-pyrimidine, are hydrolysed to water-soluble by-products, specifically to 2-hydroxy-4-(methylsulfonyl)-6-methoxy-1, 3-pyrimidine and 6-hydroxy-2-(methylsulfonyl)-4-methoxy-1,3-pyrimidine, the decrease and increase of which over time in the organic phase and in the aqueous phase, respectively, can be monitored directly, for example by GC, HPLC or TLC (Reaction Scheme 2).

A preferred aqueous base is an aqueous solution of a hydroxide, for example an alkali metal hydroxide. Preference is given to using 30% aqueous sodium hydroxide solution. Suitable water-immiscible aromatic hydrocarbons according to Variant B) are in particular toluene, and suitable water-miscible organic solvents according to Variant C) are in particular methanol and ethanol.

In the case of Variant A), after the stirring in aqueous phase (hydrolysis), it is either possible, in a Variant AB), to add a water-immiscible inert organic solvent and, if appropriate, a phase-transfer catalyst as under Variant B), or, in a Variant AC), to add a water-miscible organic solvent, as mentioned under Variant C), for easier product isolation, followed by stirring of the resultant two-phase (Variant A)+AB)) or aqueous-organic one-phase system (Variant A)+AC)) for from 5 to 15 minutes and work-up similarly to how it is described under Variant B) and C), respectively.

In the case of the two-phase system according to Variant B) or A)+AB), the aqueous phase is separated off and, for complete extraction of the desired target compound, mixed once more with the same water-immiscible organic solvent as used above, and the entire two-phase system is stirred for from 5 to 15 minutes. After cooling, the aqueous phase is separated off, the two organic phases are combined and the organic solvent is distilled off under reduced pressure. Reaction Scheme 2 illustrates this enrichment process (Variants B) and A)+AB)).

Suitable phase-transfer catalysts for Variants B) and A)+AB) are, for example, the catalysts listed in Angew. Chem., Int. Ed. Engl. 13, 170–179 (1974), in particular quaternary ammonium salts, for example tetraalkylammonium halides, and in particular tricaprylmethylammonium chloride (Aliquat 336). The phase-transfer catalysts accelerate the hydrolysis of the by-products and, as solubilizers, increase the dissolution efficiency of these hydrolysed by-products in the aqueous phase. The phase-transfer catalysts are employed in amounts of from 0.1 to 10 mol %, based on the product, 4,6-dimethoxy-2-(methylsulfonyl)-1, 3-pyrimidine.

According to Variant C) and A)+AC), the desired target compound is present as a suspension which is poorly water-soluble and can be separated off easily from the aqueous-organic phase by filtration, whereas the hydrolysed and water-soluble by-products, for example 2-hydroxy-4-(methylsulfonyl)-6-methoxy- and 6-hydroxy-2-(methylsulfonyl)-4-methoxy-1,3-pyrimidine, remain in solution.

Reaction Scheme 2 illustrates this enrichment process (Variants C) and A)+AC)).

To optimize the product yield, in Variant C) and AC), the proportion of water-miscible organic solvents added is kept just at such a level that, on the one hand, homogeneity of the reaction mixture is ensured and, on the other hand, yield losses are as low as possible. In general, the proportion of water-miscible solvents is in the range from 5 to 50% by weight, based on the amount of aqueous-acidic reaction mixture. If the concentration of water-miscible organic solvents is too high, the solubility of the target compound in the aqueous medium is increased, resulting in a reduced product yield.

In preferred Variants A), B) or C), the aqueous base used is, for example, a hydroxide, for example an alkali metal hydroxide, which is added dropwise with stirring at reaction temperatures of from 10° to 90° C. to the aqueous-acidic reaction mixture until the pH range of the reaction mixture is 5–8, and these resulting mixtures are then stirred in the temperature range and the pH range stated above for from 0.5 to 5 hours, according to Variant A) without addition of an organic solvent, according to Variant B) after addition of an organic solvent, for example an aromatic hydrocarbon, for example benzene, toluene or the isomeric xylenes, or according to Variant C) after addition of an organic solvent, for example an alcohol. Among these, preference is given to those variants in which the aqueous base used is a 30% aqueous sodium hydroxide solution, which is added dropwise at reaction temperatures of from 75° to 85° C. to the aqueous-acidic reaction mixture until the pH is 6–7, where either no organic solvent (Variant A)) or the organic solvent toluene (Variant B)) or methanol or ethanol (Variant C)) is added, and these mixtures are stirred in the temperature range of from 20° to 80° C. and in the pH range stated above for from 1 to 3 hours.

In a particularly preferred Variant B), the organic water-immiscible solvent which is added to the aqueous reaction mixture is toluene, employing, as phase-transfer catalyst, tricaprylmethylammonium chloride (Aliquat 336) in an amount of from 0.5 to 5 mol %, based on the 4,6-dimethoxy-2-(methylsulfonyl)-1,3-pyrimidine formed.

The intermediate 4,6-dimethoxy-2-(methylthio)-1,3-pyrimidine (not isolated, Reaction Scheme 1) is chemically stable and could be isolated without any problems from the reaction mixture.

Accordingly, as an alternative to the present process with an initial two-step reaction sequence for the preparation of 4,6-dimethoxy-2-(methylsulfonyl)-1,3-pyrimidine starting from 4,6-dichloro-2-(methylthio)-1,3-pyrimidine, it is also possible to use an initial one-step process in which the starting material 4,6-dimethoxyl-2-(methylthio)-1,3-pyrimidine is oxidized in an aqueous-acidic medium, if appropriate in the presence of a catalyst, wherein a purification step according to the present invention is carried out after the oxidation. The present invention also provides this alternative process.

5) it does not require a complicated recrystallization, which is associated with product loss, 6) it provides easy direct access, in an economically and ecologically advantageous manner, to 4,6-dimethoxy-2-(methylsulfonyl)-1,3-pyrimidine, and 7) it permits subsequent reactions "in situ", for example conversion into 7-[(4,6-dimethoxypyrimidin-2-yl)thio] phthalide derivatives.

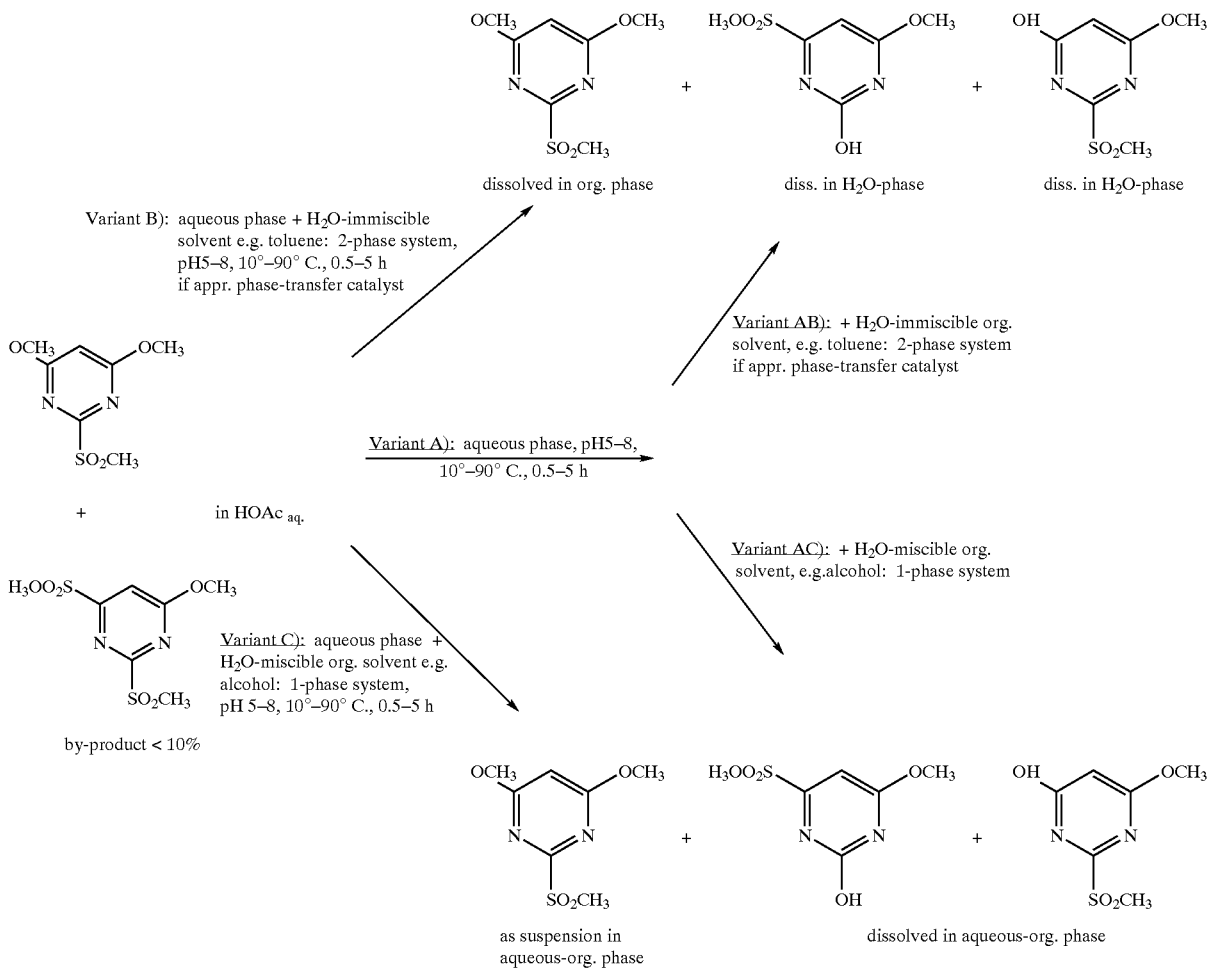

The overall yields of isolated product 4,6-dimethoxy-2-(methylsulfonyl)-1,3-pyrimidine are generally >75%, the purity of the end product being >98%.

The starting material 4,6-dichloro-2-(methylthio)-1,3-pyrimidine is known, for example, from J. Org. Chem. 26, 792 (1961). Likewise known are all of the reagents used, such as methoxides, oxidizing agents and phase-transfer catalysts, or they can be prepared by known processes.

The process according to the invention differs from the known processes in that 1) it affords the target compound 4,6-dimethoxy-2-(methylsulfonyl)-1,3-pyrimidine in high purity and yield, 2) it can be carried out in a multipurpose plant, 3) it can be carried out both continuously and batch-wise (discontinuously), 4) with respect to Step 2 (oxidation) and the purification step, it is designed as a "one-pot reaction", Accordingly, compared to the known processes, the present process has the following advantages:

1) it is particularly suitable for industrial processes, 2) it avoids complicated separation and purification steps, 3) it allows easy recycling of organic solvents (for example toluene and methanol) and/or avoids problematic waste (only water and salts, for example sodium chloride and sodium sulfate and/or sodium acetate are produced), and 4) it allows direct "in situ" further processing of the 4,6-dimethoxy-2-(methylsulfonyl)-1,3-pyrimidine formed.

The 4,6-dimethoxy-2-(methylsulfonyl)-1,3-pyrimidine prepared according to the invention is an important intermediate in the synthesis of herbicides and is used specifically as an intermediate in the preparation of herbicidal 7-[(4,6-dimethoxypyrimidin-2-yl)thio]-3-methylnaphthalide, as described, for example, in EP-B-0 447 506 and as illustrated in Reaction Scheme 1.

Reaction Scheme 1

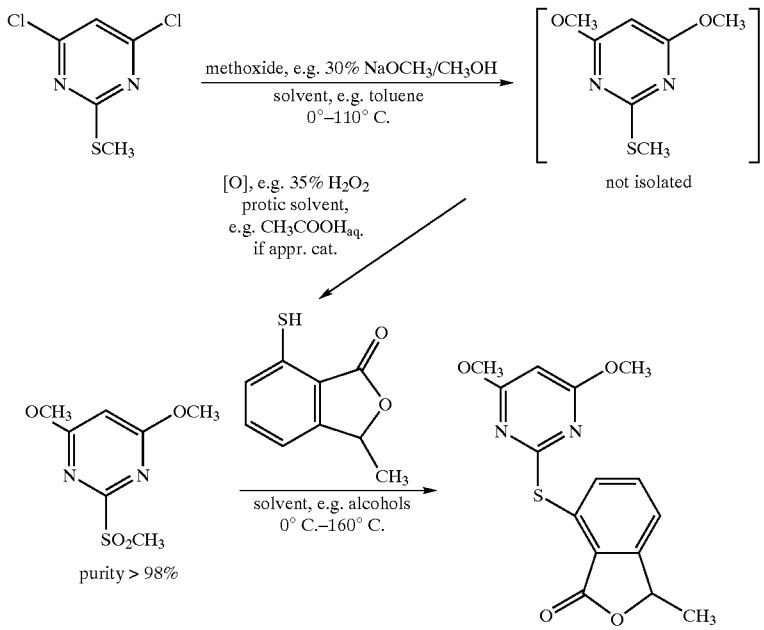

The starting material used is 4,6-dichloro-2-(methylthio)-1,3-pyrimidine which, according to Reaction Scheme 1 and as described above, is reacted in the first step in an inert organic solvent with an alkali metal methoxide to give the 4,6-dimethoxy-2-(methylthio)-1,3-pyrimidine intermediate, which is not isolated, the inert organic solvent is replaced by an aqueous-protic solvent, and, in a second step, the corresponding 4,6-dimethoxy-2-(methylsulfonyl)-1,3-pyrimidine is obtained in pure form by oxidation and a subsequent purification step designed as "one-pot reaction". The subsequent reaction of the 4,6-dimethoxy-2-(methylsulfonyl)-1,3-pyrimidine formed with 7-mercapto-3-methylnaphthalide in Reaction Scheme 1 is expediently carried out in an inert organic solvent, for example alcohols, ethers, ketones, nitriles or amides, for example isopropanol, tetrahydrofuran, butanone, acetonitrile or N,N-dimethylformamide, at temperatures of from 0° to 160° C. Such substitution reactions are described, for example, in EP-B-0 447 506.

The process according to the invention is illustrated in more detail by the example below.

EXAMPLE H1

Preparation of 4,6-dimethoxy-2-(methyl-sulfonyl)-1,3-pyrimidine

At 20°–25° C., 525.6 g of 4,6-dichloro-2-(methylthio)-1,3-pyrimidine (1.5 mol), as a solution in toluene (55.7%), are initially charged in a plane-joint flask fitted with stirrer, thermometer, dropping funnel, distillation head and pH probe, and 583.2 g of 30% sodium methoxide solution (3.24 mol) are added dropwise at 40°–42° C. over a period of 4 hours. The reaction is exothermic and forms a readily stirrable suspension (sodium chloride). After about 1 hour, the reaction temperature is increased to 54°–56° C. and the mixture is stirred at this temperature for 5–6 hours, until complete conversion is detected, for example by gas chromatography. Some of the methanol is then distilled off from the reaction mixture under reduced pressure at 60° C., until about 363 g of distillate are obtained. Subsequently, initially 360 g of toluene and then 750 g of water are added to the reaction residue, and the mixture is stirred until a temperature of 401–42° C. is reached. The mixture is allowed to stand for 15 minutes, and the aqueous phase (about 921 g) is then separated off, admixed with another 150 g of toluene and stirred at 40°–42° C. for 5 minutes. The aqueous phase is then allowed to stand for 15 minutes and then separated off and discarded, and the two toluene phases are combined and substantially evaporated under reduced pressure at 80° C. 330 g of water, preheated to 60° C., are added to the resulting residue, and the remaining toluene is distilled off azeotropically until only water can be detected in the distillate. 36 g of 100% acetic acid (0.6 mol) and 0–5 g of sodium tungstate (0.0015 mol) are then added to the toluene-free aqueous residue, and the entire mixture is heated to 78°–80° C. At this temperature, 350 g of a 35% hydrogen peroxide solution (3.6 mol) are added dropwise with vigorous stirring over a period of 4 hours. The oxidation is exothermic, and stirring is continued at 78°–80° C. for 1–2 hours until GC analysis shows complete conversion, i.e. no more 4,6-dimethoxy-2-(methyl-sulfoxide)-1,3-pyrimidine. To destroy excess oxidizing agent, 110 g of sodium hydrogen sulfite solution (40%, 0.412 mol) are added dropwise over a period of 30 minutes to the reaction mixture, until a test with KI-starch paper gives a negative result. 750 g of toluene are then added to the aqueous-acidic reaction mixture and, at 78°–80° C., 30% aqueous sodium hydroxide solution (about 130 g, 0.975 mol) are added dropwise until the pH is 6.5, and stirring is continued at 78°–80° C. for 1–3 hours until the by-product has reacted and has migrated into the aqueous phase (according to GC analysis, <0.2% of 2,4-bis(methylsulfonyl)-6-methoxy-1,3-pyrimidine is detected in the toluene phase). The reaction mixture is allowed to stand for 15 minutes, and the aqueous phase is then separated off and admixed with 150 g of toluene, and the entire mixture is stirred at 75°–80° C. for 5 minutes. To obtain good phase separation, the resulting two-phase system is allowed to stand, the aqueous phase (800 g) is separated off and discarded and the two toluene phases are combined and evaporated at 70° C. under reduced pressure until about 564 g of distillate are obtained. The desired product crystallizes even during distillation. After cooling to 0°–5° C., the mixture is filtered off and the crystalline residue is washed once with toluene, cooled to 0°–5° C. The crystalline product is dried under reduced pressure at 50° C. This gives 251.3 g of the desired 2,4-dimethoxy-2-(methylsulfonyl)-1,3-pyrimidine (76–4% of theory) of a purity of >99% (according to GC analysis, column OV 1701).

What is claimed is:

1. A process for preparing 4,6-dimethoxy-2-(methylsulfonyl)-1,3-pyrimidine by reacting 4,6-dichloro-2-(methylthio)-1,3-pyrimidine in an inert organic solvent with an alkali metal methoxide, transfer of the resulting 4,6-dimethoxy-2-(methylthio)-1,3-pyrimidine into an aqueous-acidic medium and subsequent oxidation of this compound, if appropriate in the presence of a catalyst, wherein the oxidation is followed by a purification step in which the aqueous-acidic reaction mixture is adjusted with aqueous base to a pH in the range of 5–8 and stirred either in the presence or in the absence of an organic solvent.

2. A process according to claim 1, wherein the aqueous base used is a hydroxide.

3. A process according to claim 2, wherein the hydroxide used is an alkali metal hydroxide.

4. A process according to claim 3, wherein 30% aqueous sodium hydroxide solution is used.

5. A process according to claim 1, wherein the pH range is 6–7.

6. A process according to claim 1, wherein the organic solvent is water-immiscible.

7. A process according to claim 6, wherein the organic solvent is an aromatic hydrocarbon.

8. A process according to claim 7, wherein the aromatic hydrocarbon used is benzene, toluene or the isomeric xylenes.

9. A process according to claim 8, wherein toluene is used.

10. A process according to claim 6, wherein a phase-transfer catalyst is present in amounts of from 0.1 to 10 mol %, based on the product 4,6-dimethoxy-2-(methylsulfonyl)-1,3-pyrimidine.

11. A process according to claim 10, wherein the phase-transfer catalyst used is tricaprylmethylammonium chloride (Aliquat 336).

12. A process according to claim 6, wherein the organic solvent is toluene and the phase-transfer catalyst is tricaprylmethylammonium chloride (Aliquat 336), used in amounts of from 0.5 to 5 mol %, based on the product formed.

13. A process according to claim 1, wherein the organic solvent is water-miscible.

14. A process according to claim 13, wherein the organic solvent is an alcohol.

15. A process according to claim 14, wherein the alcohol used is methanol or ethanol.

16. A process according to claim 1, wherein the aqueous base used is an alkali metal hydroxide, which is added dropwise with stirring at reaction temperatures of from 10° to 90° C. to the aqueous-acidic reaction mixture until the pH of the reaction mixture is 5–8, and this mixture is stirred without addition of an organic solvent (Variant A)) in the temperature range and at the pH stated above for from 0.5 to 5 hours.

17. A process according to claim 16, wherein the aqueous base used is 30% aqueous sodium hydroxide solution, which is added dropwise at reaction temperatures of from 75° to 85° C. to the aqueous-acidic reaction mixture until the pH is 6–7, and this mixture is stirred in the temperature range of from 20° to 80° C. and at the pH stated above for from 1 to 3 hours.

18. A process according to claim 1, wherein the aqueous base used is an alkali metal hydroxide, which is added dropwise with stirring at reaction temperatures of from 10° to 90° C. to the aqueous-acidic reaction mixture until the pH of the reaction mixture is 5–8, an organic solvent is added and this mixture is stirred in the temperature range and at the pH stated above for from 0.5 to 5 hours.

19. A process according to claim 18, wherein the aqueous base used is 30% aqueous sodium hydroxide solution, which is added dropwise at reaction temperatures of from 75° to 85° C. to the aqueous-acidic reaction mixture until the pH is 6–7, and the organic solvent added is either toluene or methanol or ethanol, and this mixture is stirred in the temperature range of from 20° to 80° C. and at the pH stated above for from 1 to 3 hours.

20. A process according to claim 13, wherein the organic water-miscible solvent is added in a proportion of 5–50% by weight, based on the aqueous-acidic reaction mixture.

21. A process according to claim 1, wherein the intermediate 4,6-dimethoxy-2-(methylthio)-1,3-pyrimidine is not isolated.

22. A process according to claim 1, wherein the oxidation and the purification step are carried out in the same reaction vessel as a "one-pot reaction".

23. A process for preparing 4,6-dimethoxy-2-(methylsulfonyl)-1,3-pyrimidine by oxidation of 4,6-dimethoxy-2-(methylthio)-1,3-pyrimidine in aqueous-acidic medium, if appropriate in the presence of a catalyst, wherein a purification step according to claim 1 follows.

* * * * *